United States Patent [19]
Etzbach et al.

[11] Patent Number: 5,886,242
[45] Date of Patent: Mar. 23, 1999

[54] POLYMERIZABLE, CHIRAL COMPOUNDS AND THEIR USE

[75] Inventors: Karl-Heinz Etzbach, Frankenthal; Paul Delavier, Mundenheimer; Karl Siemensmeyer, Frankenthal; Gerhard Wagenblast, Wachenheim; Lothar Laupichler, Heidelberg; Volkmar Vill, Hamburg, all of Germany

[73] Assignee: BASF Aktiengesellschaft, Ludwigshafen, Germany

[21] Appl. No.: 6,003

[22] Filed: Jan. 12, 1998

Related U.S. Application Data

[62] Division of Ser. No. 647,900, filed as PCT/EP94/04055, Dec. 6, 1994, Pat. No. 5,780,629.

[30] Foreign Application Priority Data

Dec. 11, 1993 [DE] Germany .......................... 43 42 280.2

[51] Int. Cl.$^6$ .......................... C07C 13/465; C07C 13/48; C07C 15/12; C07C 239/26
[52] U.S. Cl. .................. 585/25; 585/26; 585/27; 544/224; 544/242; 546/249; 548/136; 548/143; 549/29; 252/299.01; 252/299.61; 252/299.62; 252/299.66; 570/125; 570/127; 570/182; 570/183; 568/924; 568/928; 568/929
[58] Field of Search ...................................... 544/224, 242; 546/249; 548/136, 143; 549/29; 585/25, 26, 27; 252/299.01, 299.61, 299.62, 299.66

[56] References Cited

U.S. PATENT DOCUMENTS 5,011,623  4/1991  Yoshinaga et al. ................... 252/299.5

OTHER PUBLICATIONS

Liquid Crystals and Plastic Crystals, vol. 1, pp. 18–62, 1994, A. Saupe, "Classification and Organization of Mesomorphous Phases Formed by Non–Amphiphilic and Amphiphilic Compounds".

Festkoerper Probleme XI, pp. 99–133, 1971, H. Baessler, "Liquid Crystals ".

The Journal of Chemical Physics, vol. 52, pp. 631–637, Jan. 1—Jun. 15, 1970, H. Baessler, et al., "Helical Twisting Power of Steroidal Solutes in Cholesteric Mesophases".

The Journal of Chemical Physics, vol. 51, No. 8, pp. 3213–3218, Oct. 15, 1969, H. Baessler, et al. "Electric Field on the Optical Rotatory Power of a Compensated Cholesteric Liquid Crystal".

Zeitschrift Fuer Naturforschung, vol. 28, pp. 799–800, 1973, H. Finkelmann, et al., "AB–Initio Study of Hydrogen Bonded Radical"—Abstract only.

Die Naturwissenschaften, vol. 58, pp. 599–602. 1971, H. Stegemeyer, et al., "Induzierung Von Optischer Aktivaet Und Zirkulardichroismus in Namatischen Phasen Durch Chirale Molekuele"—Abstract only.

Berichte Der Bunsen–Gesellschaft fuer Physikalische Chemie, vol. 78. No. 7, pp 869–874, 1974, V.H. Finkelmann, et al. "Beschreibung Cholesterischer Mischsysteme Mit Einer Erweiterten Goosens–Theorie".

Molecular Crystals and Liquid Crystals, vol. 16, pp. 33–37, 1972, J. Adams, et al., "The Relationship Between Pitch Change and Stimulus in Cholesterics".

Macromolecular Chemistry and Physics, vol. 187, pp., 289–296, 1986, G. Galli, "Systhesis and Theromotropic Properties of New Mesogenic Diacrylate Monomers".

Ferroelectric Liquid Crystal Mixtures with Carbohydrate Derivatives as Dopants, Vill. V. et al,; Z. Naturforsch,.; A. Phys. Sci. (1989), 44(7), pp. 675–679. —Abstract only.

"Helical Twisting Power of Carbohydrate Derivatives," V. Vill et al, Z. Naturforsh, A. Phys. Sci. (1988), 43(12), pp. 1119–1125.—Abstract only.

Organic Chemistry, A Short Course, Hart, Hart and Crane, Hougton Mifflin Co., Boston, MA 1995, pp. 34–38.

*Primary Examiner*—Johann Richter
*Assistant Examiner*—Jane C. Oswecki
*Attorney, Agent, or Firm*—Oblon, Spivak, McClelland, Maier & Neustadt, P.C.

[57] ABSTRACT

The invention relates to chiral compounds containing at least one divalent or polyvalent chiral group, at least one polymerizable group, at least one spacer and at least one mesogenic group, and to their use as polymerizable, chiral dopes for the preparation of cholesteric networks.

The novel compounds are suitable for use in electro-optical displays or as chiral dopes for nematic or cholesteric liquid crystals in order to produce layers which reflect in colors.

7 Claims, No Drawings

POLYMERIZABLE, CHIRAL COMPOUNDS AND THEIR USE

This application is a Division of application Ser. No. 08/647,900, filed on Jun. 6, 1996, now U.S. Pat. No. 5,780,629, which was filed as International Application No. PCT/EP94/04055, filed Dec. 6, 1994.

It is known that molecules which are anisotropic in shape can form liquid-crystalline phases, known as mesophases, on warming. The individual phases differ through the spatial arrangement of the major parts of the molecules on the one hand and through the molecular arrangement with respect to the long axes on the other hand (G. W. Gray, P. A. Winsor, Liquid Crystals and Plastic Crystals, Ellis Horwood Limited, Chichester, 1974). The nematic liquid-crystalline phase is distinguished by the fact that there is only one alignment long-distance ordering due to the long molecular axes lining up in parallel. Under the prerequisite that the molecules making up the nematic phase are chiral, a cholesteric phase forms, in which the long axes of the molecules form a helical superstructure perpendicular thereto (H. Baessler, Festkörperprobleme XI, 1971). The chiral moiety may be present in the liquid-crystalline molecule itself or added to the nematic phase as a dope. Phases produced by doping are known as induced cholesteric phases. This phenomenon was first studied on cholesterol derivatives (H. Baessler, M. M. Labes, J. Chem. Phys. 52 (1970) 631; H. Baessler, T. M. Laronge, M. M. Labes. J. Chem. Phys. 51 (1969) 3213; H. Finkelmann, H. Stegemeyer, Z. Naturforschg. 28a (1973) 799). The induction of cholesteric phases later also became possible through addition of other chiral substances which themselves are not liquid-crystalline (H. Stegemeyer, K. J. Mainusch, Naturwiss. 58 (1971) 599; H. Finkelmann, H. Stegemeyer, Ber. Bunsenges. Phys. Chem. 78 (1974) 869).

The cholesteric phase has remarkable optical properties: large optical rotation and pronounced circular dichroism caused by selective reflection of circular-polarized light within the cholesteric layer. The different colors to be observed depending on the viewing angle depend on the pitch of the helical superstructure, which is itself dependent on the twisting power of the chiral component. The pitch and thus the wavelength range of the selectively reflected light of a cholesteric layer can be varied, in particular, by changing the concentration of a chiral dope (J. E. Adams, W. E. L. Haas, Mol. Cryst. Liq. Cryst. 16 (1972) 33). Such cholesteric systems offer interesting opportunities for practical use. Thus, incorporation of chiral moieties into mesogenic acrylic esters after alignment in the cholesteric phase and photocrosslinking can give a stable, colored network, but the concentration of the chiral component therein cannot be changed (G. Galli, M. Laus, A. Angeloni, Makromol. Chem. 187 (1986) 289). Furthermore, admixing of non-crosslinkable, chiral compounds with nematic acrylic esters after photocrosslinking can give a colored polymer (I. Heynderickx, D. J. Broer, Mol. Cryst. Liq. Cryst. 203 (1991) 113), but this still contains volatile constituents which prevent use.

It is an object of the present invention to provide novel chiral compounds which firstly have a high twisting power and secondly can be incorporated in a stable manner into the cholesteric phase in any desired concentration without diffusing out of the phase or crystallizing.

We have found that this object is achieved by polymerizable, chiral compounds.

The present invention accordingly provides polymerizable, chiral compounds containing at least one divalent or polyvalent chiral group, at least one polymerizable group, at least one spacer and at least one mesogenic group, and to their use as polymerizable, chiral dopes for the preparation of cholesteric networks.

The polymerizable groups here are, in particular, vinyl radicals, which are present, for example, in acrylic compounds, vinyl ethers or styrene derivatives. Epoxides are also suitable.

Chiral groups which are suitable for the novel compounds are derived, in particular, from sugars, bifunctional or polyfunctional compounds from the biphenyl or binaphthyl series, optically active glycols, dialcohols or amino acids.

The spacers and mesogenic groups are the radicals conventionally used for this purpose.

The groups necessary for the novel compounds are linked to one another via bridges, such as O, COO, OCO, CONH, NRCO, CON(R), N(R)CO or a direct bond.

In particular, the present invention provides compounds of the formula I

where, in each case independently of one another,

A is a spacer,

M is a mesogenic group,

Y is a direct bond, O, S, COO, OCO, CON(R) or N(R)CO,

Z is a polymerizable group, n is a number from 2 to 6,

X is a chiral radical and

R is $C_1$- to $C_4$-alkyl or hydrogen.

The spacers A can be any groups known for this purpose; the spacers are usually linked to X via ester or ether groups or a direct bond. The spacers generally contain from 2 to 30, preferably from 2 to 12, carbon atoms and may be interrupted in the chain, for example by O, S, NH or $NCH_3$. Possible substituents for the spacer chain are fluorine, chlorine, bromine, cyano, methyl or ethyl.

Examples of representative spacers are:

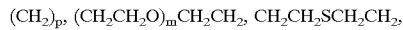

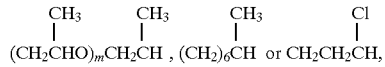

where m is from 1 to 3 and p is from 1 to 12.

The radicals M can again be the known mesogenic groups. Particularly suitable are radicals containing cycloaliphatic, aromatic or heteroaromatic groups. The mesogenic radicals conform, in particular, to the formula II

where each T, independently of the others, is cycloalkylene, an aromatic radical or a heteroaromatic radical, each $Y^1$, independently of the others, is O, COO, OCO, $CH_2O$, $OCH_2$, CH=N, N=CH or a direct bond, and r is from 0 to 3.

r is preferably 0 or 1.

T is generally a non-aromatic or aromatic, carbocyclic or heterocyclic ring system, which is unsubstituted or substituted by fluorine, chlorine, bromine, cyano, hydroxyl or nitro, and which conforms, for example, to one of the following basic structures:

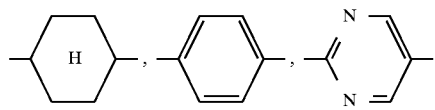

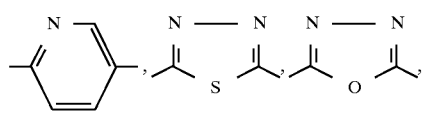

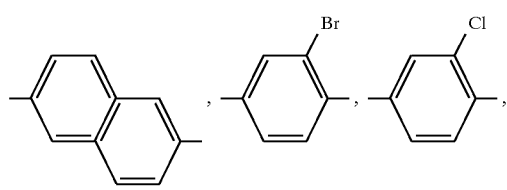

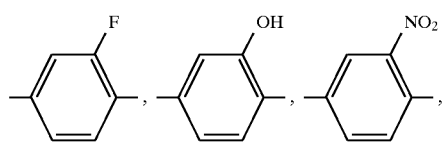

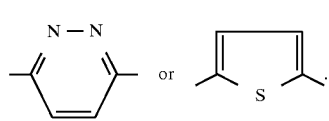

Particularly preferred mesogenic groups M are, for example:

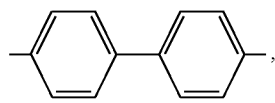

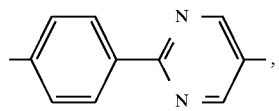

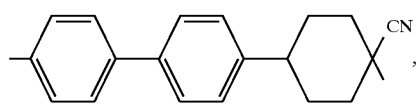

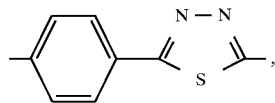

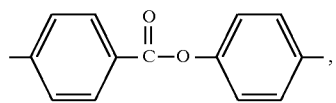

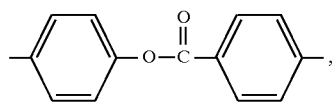

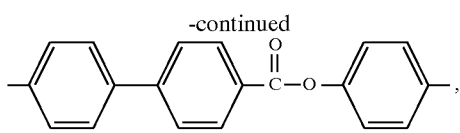

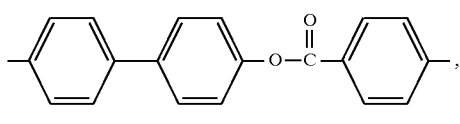

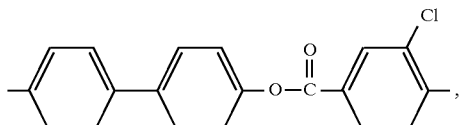

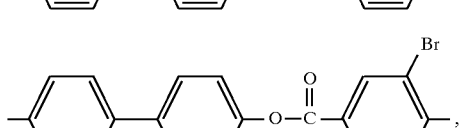

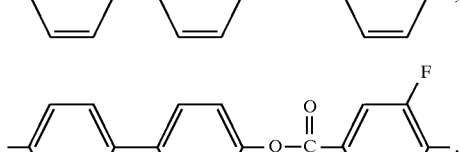

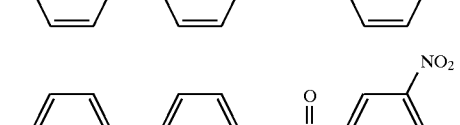

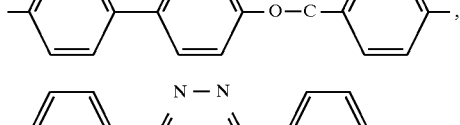

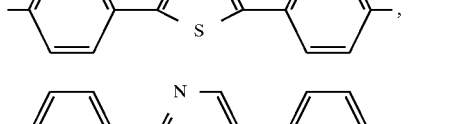 or

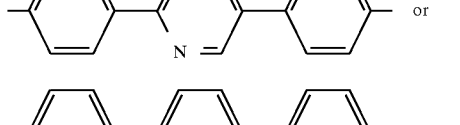

n in the formula I is preferably 2 or 3, in particular 2.

Of the chiral radicals X, availability means that particular preference is given to those derived from sugars, binaphthyl or biphenyl derivatives or optically active glycols or dialcohols. In the case of sugars, particular mention may be made of pentoses and hexoses, and derivatives thereof.

Examples of individual radicals X are:

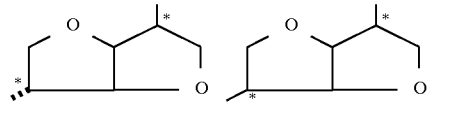

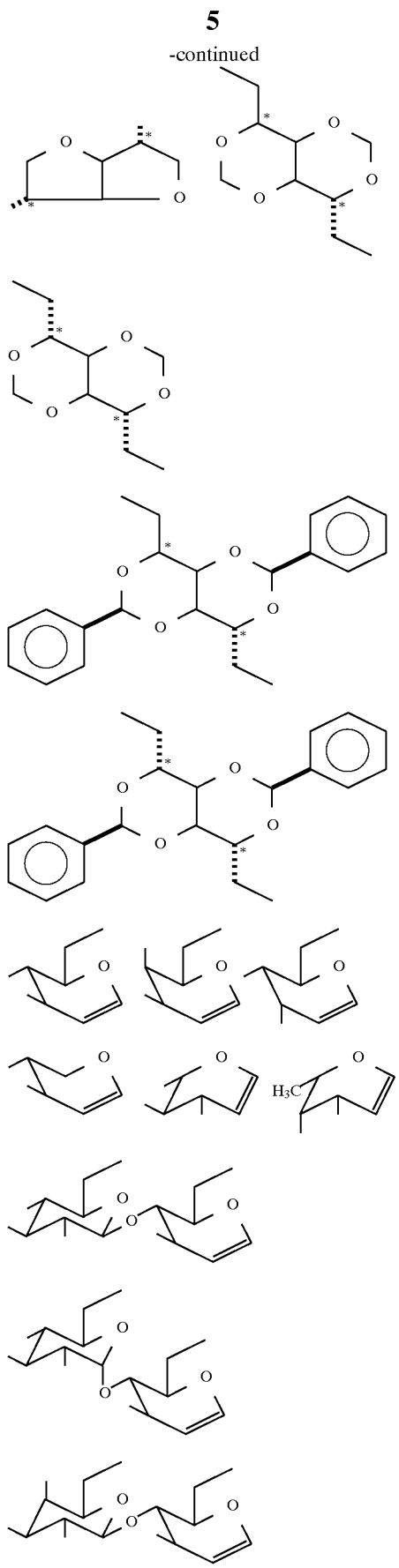
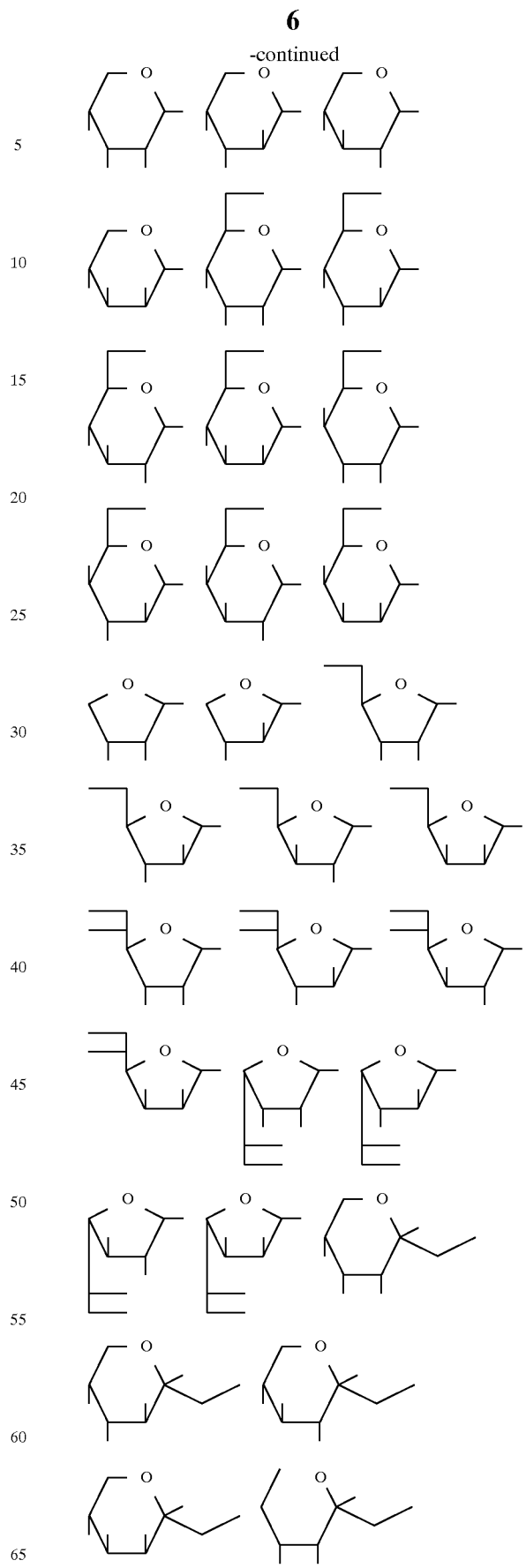

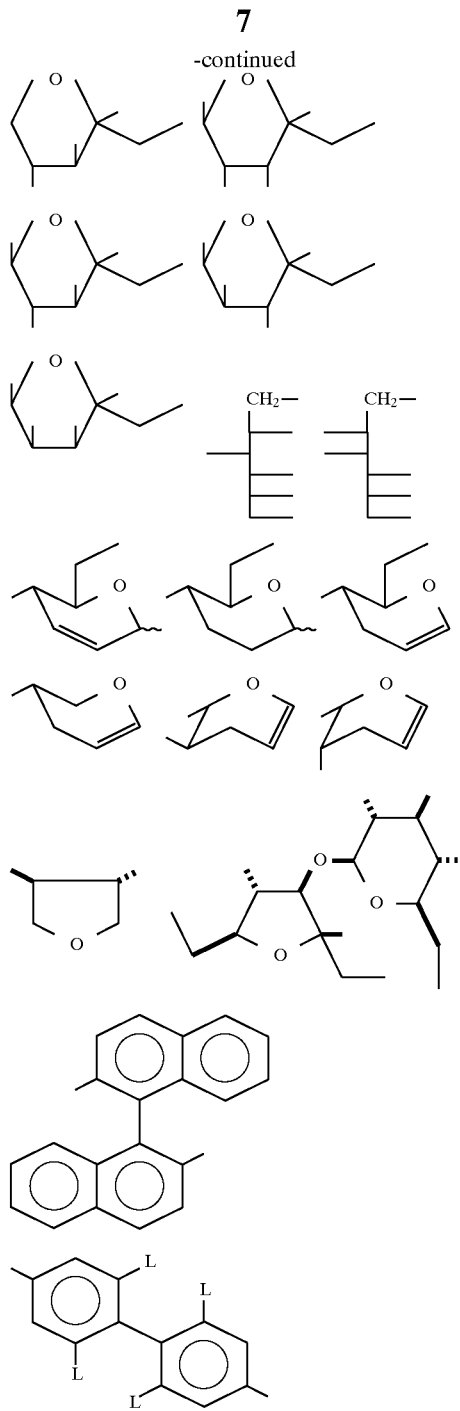

where

L is $C_1$- to $C_4$-alkyl, $C_1$–$C_4$-alkoxy, halogen, COOR, OCOR, CONHR or NHCOR, where R is as defined above.

Particular preference is given to, for example,

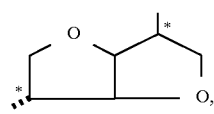

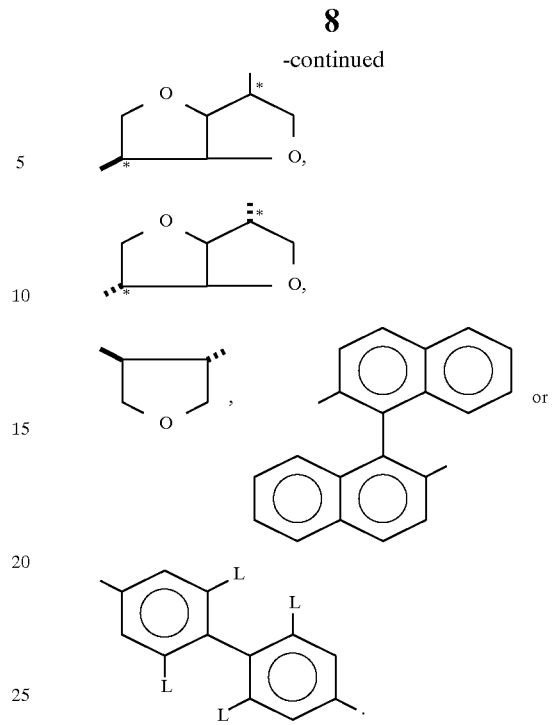

Optically active glycols or derivatives thereof correspond, for example, to the formula

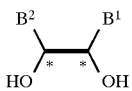

where $B^1$ and $B^2$, independently of one another, are $C_1$ to $C_4$-alkyl, which may be substituted by hydroxyl and interrupted by —O—, or are phenyl or substituted or unsubstituted carboxyl, and one of the radicals is alternatively hydrogen, where, in the case of identical radicals $B^1$ and $B^2$, the configuration R, S is excluded.

Individual such radicals $B^1$ and $B^2$ are, for example,

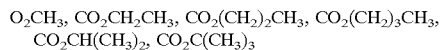

or

Also suitable are specific bifunctional chiral groups which have the following structures:

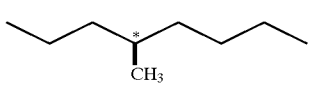

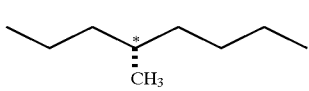 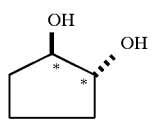

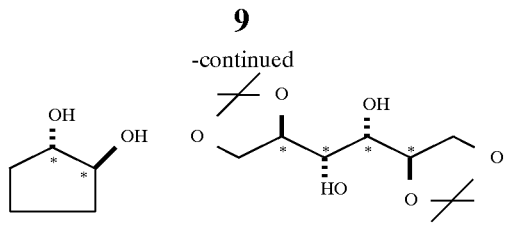

Examples of preferred radicals Z are:

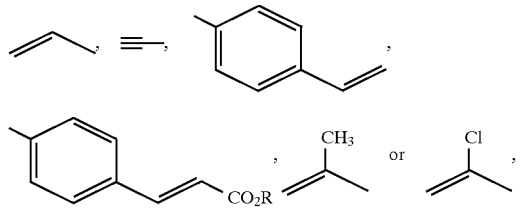

where R is as defined above.

The units Z—Y—A—Y—M—Y according to the invention, where Z, Y, A and M are as defined above, can be obtained by synthetic methods which are known in general terms, as described, for example, in DE-A 39 17 196.

The chiral moieties can be obtained commercially and are thus available.

The novel compounds are particularly suitable for use in electro-optical display elements or as chiral dopes for nematic or cholesteric liquid crystals in order to produce layers which reflect in colors.

EXAMPLE 1

2,5-Bis[4'-(2-acryloyloxyethoxy)biphenyl-4-carbonyloyl]-1,4;3,6-dianhydro-D-sorbitol

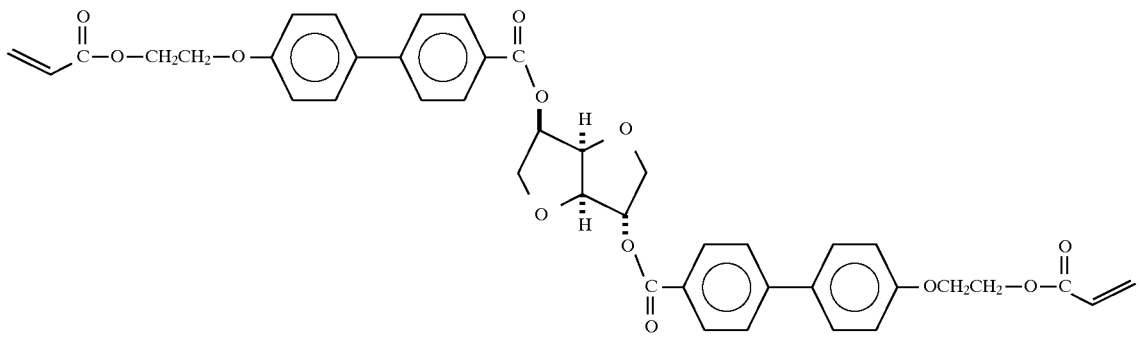

a Ethyl 4'-hydroxyethoxybiphenyl-4-carboxylate

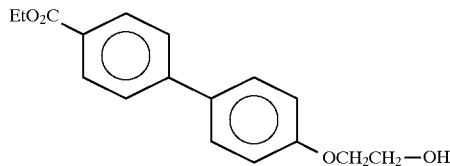

72.6 g (0.3 mol) of ethyl 4'-hydroxybiphenyl-4-carboxylate are dissolved in 225 ml of absolute dimethylformamide, and 45.5 g (0.33 mol) of potassium carbonate and 3.0 of potassium iodide are added. 26.57 g (0.33 mol) of 2-chloroethanol are then added, and the mixture is heated at 100° C. for 5 hours. After the mixture has been stirred overnight at room temperature, a further 22.77 g (0.17 mol) of potassium carbonate and 13.3 g (0.17 mol) of 2-chloroethanol are added. The mixture is heated at 100° C. for a further 15 hours, cooled and precipitated in water. The solid residue is washed with water to neutral and dried. The moist product can immediately be reacted further.

Yield: 123 g of moist product, m.p. (pure substance) 128°–129° C.

b 4'-Hydroxyethoxybiphenyl-4-carboxylic acid

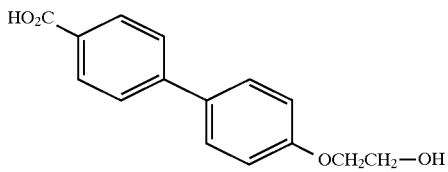

123 g (about 0.3 mol) of water-moist ethyl 4'-hydroxyethoxybiphenyl-4-carboxylate are dissolved in 258 ml of ethanol, and 67.22 g (0.6 mol) of 50% strength KOH solution are added. The mixture is refluxed for one hour and cooled, and the residue is filtered off, washed with ethanol and sucked dry. The crude product is stirred in water and acidified with dilute hydrochloric acid. After the mixture has been stirred for a number of hours, the product is filtered off with suction, washed with water to neutral and dried.

Yield: 68.0 g=88%, m.p. 155° C.

c 4'-(2-Acryloyloxyethoxy)biphenyl-4-carboxylic acid

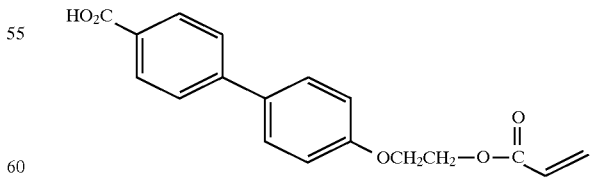

38.7 g (0.15 mol) of 4'-hydroxyethoxybiphenyl-4-carboxylic acid are dissolved in 220 ml of 1,1,1-trichloroethane, and 54.0 g (0.75 mol) of freshly distilled acrylic acid and 0.5 g of hydroquinone are added. 10.0 g of p-toluenesulfonic acid are added, and the mixture is refluxed on a water separator for 4 hours. A further 54.0 g (0.75 mol)

of distilled acrylic acid are then added, and the mixture is heated for a further 3.5 hours until everything is dissolved. The mixture is cooled, the residue is filtered off with suction, washed with 1,1,1-trichloroethane and subsequently stirred with t-butyl methyl ether and water. The solid residue is filtered off with suction, washed with t-butyl methyl ether, dried and recrystallized from 1.4 l of ethyl acetate.

Yield: 19.0 g≙41%.

d 2-(4'-Chlorocarbonylbiphenyl-4-yloxy)ethyl acrylate

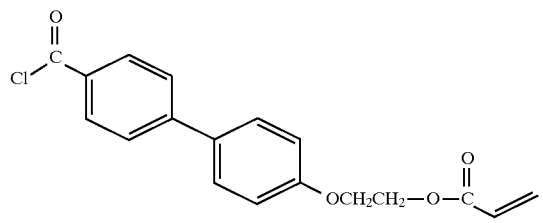

9.36 g (0.03 mol) of 4'-(2-acryloyloxyethoxy)biphenyl-4-carboxylic acid are introduced into 25 ml of oxalyl chloride, and one drop of dimethylformamide is added. A spatula tip of 2,6-di-t-butylmethylphenol is added as free-radical inhibitor, and the reaction mixture is then heated at 40°–50° C. for 35 minutes. The excess oxalyl chloride is subsequently removed by distillation in a water-pump vacuum, and the oily residue which remains is dried overnight in an oil-pump vacuum. The product can be processed further directly.

Yield: 10.1 g≙99%.

e 2,5-Bis[4'-(2-acryloyloxyethoxy)biphenyl-4-carbonyloyl]-1,4;3,6-dianhydro-D-sorbitol 1.99 g (0.014 mol) of 1,4;3,6-dianhydro-D-sorbitol are dissolved in 50 ml of absolute dichloromethane, and 2.37 g (0.03 mol) of absolute pyridine and a spatula tip of 2,6-di-t-butylmethylphenol are then added, and subsequently 9.93 g (0.03 mol) of 2-(4'-chlorocarbonylbiphenyl-4-yloxy)ethyl acrylate dissolved in 20 ml of absolute dichloromethane are added dropwise at 0°–5° C. The mixture is stirred overnight with slow warming, water and a little dilute hydrochloric acid are then added, and the mixture is extracted a number of times with ether. The combined organic phases are washed with water, dried using $Na_2SO_4$ and freed from solvent. The product is purified by column chromatography (silica gel, eluent: toluene/ethyl acetate 8:2).

Yield: 0.91 g≙9%, m.p.>175° C.

$^1$H-NMR (200 MHz, $CDCl_3$): δ=4.11 (d, J=6.3 Hz, 2H, —$CH_2$—, ring H), 4.15 (m, 2H, —$CH_2$—, ring H), 4.25 (t, J=6 Hz, 4H, —$CH_2$—OAr), 4.55 (t, J=6 Hz, 4H, —$CH_2$—OCOR), 4.75 (d, J=6 Hz, 1H, bridge H). 5.13 (t, J=6 Hz, 1H, bridge H), 5.45 (q, J=6 Hz, 1H, ring H), 5.55 (m, 1H, ring H), 5.88 (d, J=10.6 Hz, 2H, olef. H), 6.20 (dd, J=17 Hz, J'=10.6 Hz, 2H, olef. H), 7.0 (d, J=8.6 Hz, 4H, arom. H), 7.5–7.7 (m, 8H, arom. H), 8.06 (d, J=8.6 Hz, 2H, arom. H), 8.13 (d, J=8.6 Hz, 2H, arom. H).

EXAMPLE 2

2,5-Bis[4'-(2-acryloyloxyethoxy)phenyl-4-carbonyloyl]-1,4;3,6-dianhydro-D-sorbitol The compound was prepared by a method similar to that of Example 1 using ethyl 4-hydroxybenzoate.

Yield: 1.24 g≙16%, m.p.>156° C.

$^1$H-NMR (200 MHz, $CDCl_3$): δ=4.05 (d, J=5.7 Hz, 2H, —$CH_2$—, ring H), 4.12 (m, 2H, —$CH_2$—, ring H), 4.24 (t, J=6 Hz, 4H, —$CH_2$—OAr), 4.56 (t, J=6 Hz, 4H, —$CH_2$—OCOR), 4.70 (d, J=6 Hz, 1H, bridge H), 5.08 (t, J=6 Hz, 1H, bridge H), 5.40 (q, J=6 Hz, 1H, ring H), 5.46 (m, 1H, ring H), 5.82 (d, J=10.7 Hz, 2H, olef. H), 6.18 (dd, J=17 Hz, J'=10.7 Hz, 2H, olef. H), 6.48 (d, J=17 Hz, 2H, olef. H), 6.95 (d, J=8.3 Hz, 2H, arom. H), 7.0 (d, J=8.3 Hz, 2H, arom. H), 7.95 (d, J=8.3 Hz, 2H, arom. H), 8.05 (d, J=8.3 Hz, 2H, arom. H).

EXAMPLE 3

2,5-Bis[4'-(2-acryloyloxyethoxy)biphenyl-4-carbonyloyl]-1,4;3,6-dianhydro-D-mannitol

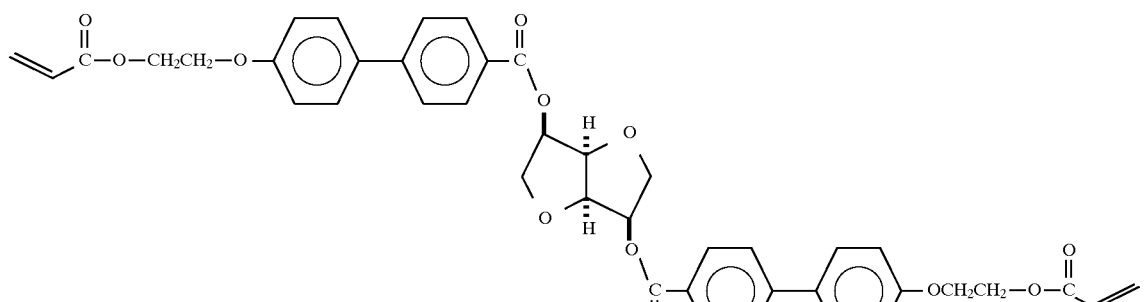

The compound was prepared by a method similar to that of Example 1 using 1,4;3,6-dianhydro-D-mannitol.

Yield: 1.18 g≈12%, m.p.>195° C.

$^1$H-NMR (200 MHz, CDCl$_3$): δ=3.82 (dd, J=6.3 Hz, J'=3 Hz, 2H, —CH$_2$—, ring H), 3.88 (dd, J=6.3 Hz, J'=3 Hz, 2H, —CH$_2$—, ring H), 4.15 (t, J=6 Hz, 4H, —CH$_2$—OAr), 4.4 (t, J=6 Hz, 4H, —CH$_2$—OCOR), 4.8 (m, 2H, bridge H), 5.25 (m, 1H, bridge H), 5.35 (m, 1H, ring H), 5.85 (d, J=10.4 Hz, 2H, olef. H), 6.15 (dd, J=16 Hz, J'=10.4 Hz, 2H, olef. H), 6.4 (d, J=16 Hz, 2H, olef. H), 7.1 (d, J=8.5 Hz, 4H, arom. H), 7.55 (d, J=8.5 Hz, 4H, arom. H), 8.0 (d, J=8.5 Hz, 4H, arom. H), 8.1 (d, J=8.5 Hz, 4H, arom. H).

$^1$H-NMR (200 MHz, CDCl$_3$): δ=3.93 (dd, J=11.0 Hz, J'=3.0 Hz, 2H, —CH$_2$—, ring H), 3.98 (dd, J=11.0 Hz, J'=3 Hz, 2H, —CH$_2$—, ring H), 4.30 (t, J=6 Hz, 4H, —CH$_2$—OAr), 4.50 (t, J=6 Hz, 4H, —CH$_2$—OCOR), 5.35 (s, 2H, bridge H), 5.65 (dd, J=11.0 Hz, J'=3 Hz, 2H, bridge H), 5.90 (d, J=10.7 Hz, 2H, olef.H), 6.20 (dd, J=16.0 Hz, J'=10.7 Hz, 2H, olef. H), 6.55 (d, J=16 Hz, 2H, olef. H), 7.1 (d, J=8.7 Hz, 4H, arom. H), 7.50 (d, J=8.7 Hz, 4H, arom. H), 8.12 (d, J=8.7 Hz, 4H, arom. H), 8.13 (d, J=8.7 Hz, 4H, arom. H).

EXAMPLE 4

2,5-Bis[4'-(2-acryloyloxyethoxy)biphenyl-4-carbonyloyl]-1,4;3,6-dianhydro-L-iditol

EXAMPLE 5

2,5-Bis[4'-(2-acryloyloxyethoxy)biphenyl-4-carbonyloyl]-1,4;3,6-dianhydro-L-iditol

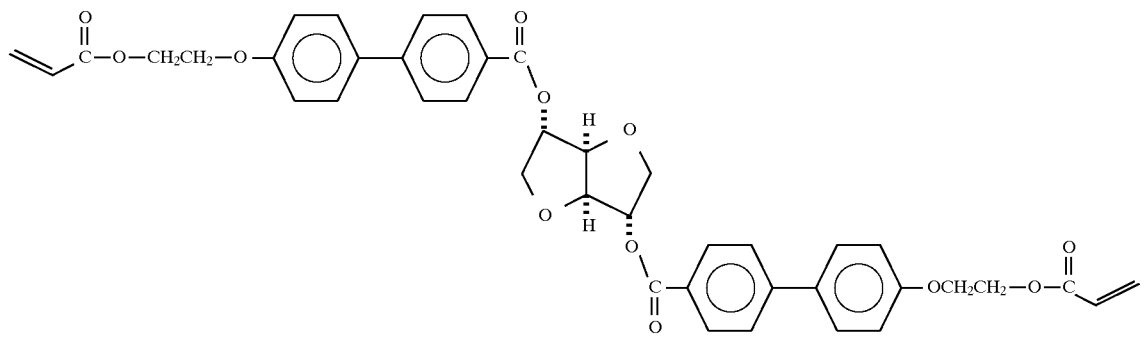

The compound was prepared by a method similar to that of Example 1 using 1,4;3,6-dianhydro-L-iditol.

Yield: 1.89 g≈19%, m.p.>195° C.

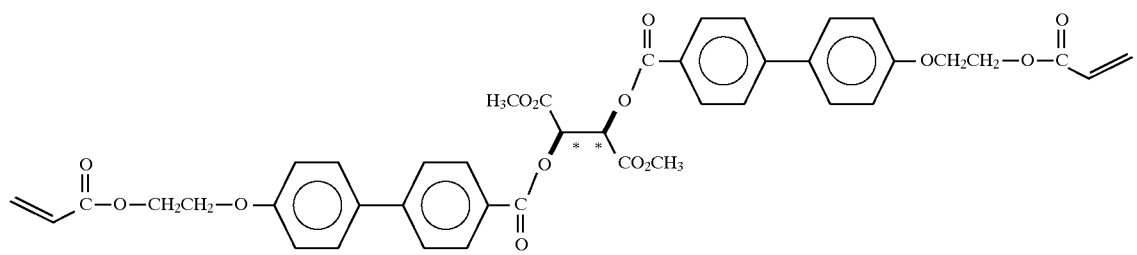

The compound was prepared by a method similar to that of Example 1 using diethyl (R,R)-tartrate.

Yield: 2.22 g≙20%, m.p. 146° C.

$^1$H-NMR (200 MHz, CDCl$_3$): δ=1.28 (t, J=6.9 Hz, 6H, ester CH$_3$), 4.15 (q, J=6.9 Hz, 4H, ester CH$_2$), 4.3 (t, J=6.0 Hz, 4H, —CH$_2$—O—arom.), 4.55 (t, J=6.0 Hz, 4H, —CH$_2$—O—COR), 5.88 (d, J=11.3 Hz, 2H, olef. H), 6.04 (s, 2H, —CH(OR)(CO$_2$R)), 6.16 (dd, J=17.3, J'=11.3 Hz, 2H, olef. H), 6.48 (d, J=17.3 Hz, 1H, olef. H), 7.05 (d, J=8.6 Hz, 4H, arom. H), 7.57 (d, J=8.6 Hz, 4H, arom. H), 7.68 (d, J=7.6 Hz, 4H, arom. H), 8.16 (d, J=7.6 Hz, 4H, arom. H).

The compounds shown in the tables below, which have similar physical properties, can also be prepared by methods similar to those described.

TABLE 1 chiral radical:

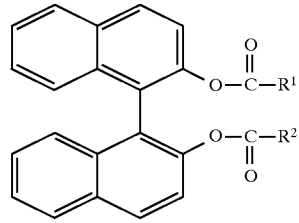

| Example | |
|---|---|
| 7 | 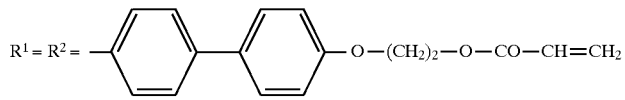 |
| 8 | 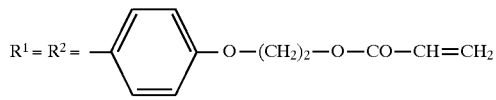 |
| 9 | 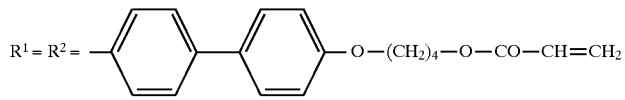 |
| 10 | 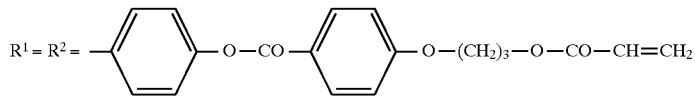 |
| 11 | 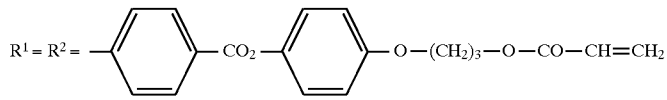 |
| 12 | 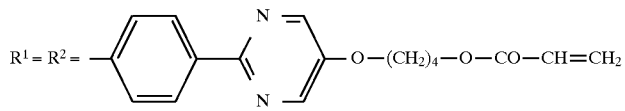 |
| 13 | 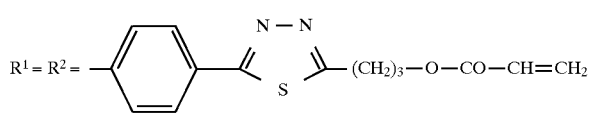 |
| 14 | R$^1$, R$^2$ random mixture of the radicals from Examples 7, 10 and 12, employed in the ratio 1:1:1. |

TABLE 2
chiral radical:
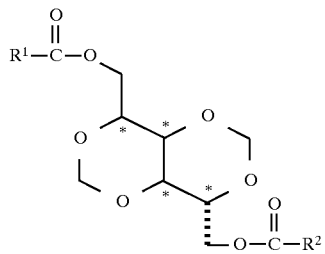
| Example | |
|---|---|
| 15 | 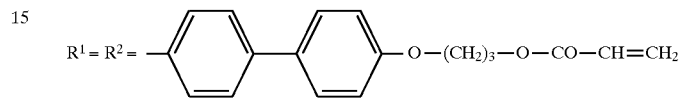 $R^1 = R^2 =$ |
| 16 | 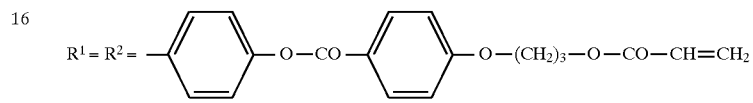 $R^1 = R^2 =$ |
| 17 | 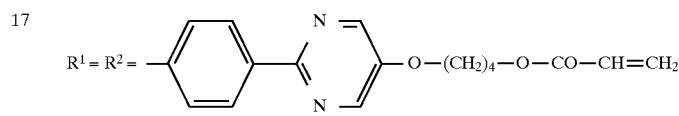 $R^1 = R^2 =$ |
| 18 | 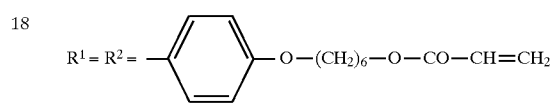 $R^1 = R^2 =$ |
| 18 |  $R^1 = R^2 =$ |
TABLE 3
chiral radical:
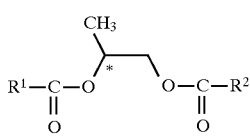
| Example | |
|---|---|
| 20 |  $R^1 = R^2 =$ |
| 21 | 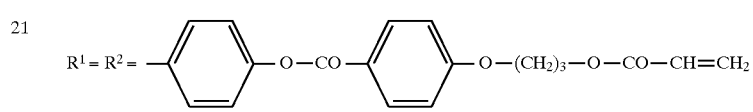 $R^1 = R^2 =$ |
| 22 | $R^1$, $R^2$ random mixture of the radicals from Examples 9, 11 and 13, employed in the ratio 1:1:1. |

TABLE 4 chiral radical:

$$R^1-\underset{\underset{O}{\|}}{C}-O-\overset{CH_3}{\underset{*}{C}H}-\overset{CH_3}{\underset{*}{C}H}-O-\underset{\underset{O}{\|}}{C}-R^2$$

| Example | |
|---|---|
| 23 | $R^1 = R^2 =$ —[biphenyl]—O—(CH$_2$)$_2$—O—CO—CH=CH$_2$ |
| 24 | $R^1 = R^2 =$ —[phenyl]—O—CO—[phenyl]—O—(CH$_2$)$_3$—O—CO—CH=CH$_2$ |
| 25 | $R^1 = R^2 =$ —[bicyclohexyl]—O—(CH$_2$)$_4$—O—CO—CH=CH$_2$ |
| 26 | $R^1 = R^2 =$ —[phenyl]—[N=N / S thiadiazole]—(CH$_2$)$_3$—O—CO—CH=CH$_2$ |
| 27 | $R^1 = R^2 =$ —[phenyl]—O—(CH$_2$)$_2$—O—CO—CH=CH$_2$ |
| 28 | $R^1$, $R^2$ random mixture of the radicals from Examples 23 and 25, employed in the ratio 2:1. |

TABLE 5 chiral radical:

$$R^1-\underset{\underset{O}{\|}}{C}-O \diagdown \text{(sugar ring, *)} \diagup O-\underset{\underset{O}{\|}}{C}-R^3$$
$$R^2-\underset{\underset{O}{\|}}{C}-O \diagup$$

| Example | |
|---|---|
| 29 | $R^1 = R^2 = R^3 =$ —[biphenyl]—O—(CH$_2$)$_2$—O—CO—CH=CH$_2$ |
| 30 | $R^1 = R^2 = R^3 =$ —[phenyl]—O—CO—[phenyl]—O—(CH$_2$)$_3$—O—CO—CH=CH$_2$ |
| 31 | $R^1$, $R^2$, $R^3$ random mixture of the radicals from Examples 7, 10 and 12, employed in the ratio 1:1:1. |

TABLE 6 chiral radical:

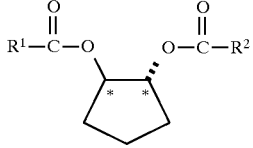

| Example | |
|---|---|
| 32 | $R^1 = R^2 =$ 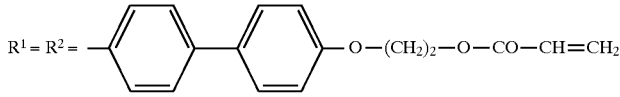 |
| 33 | $R^1 = R^2 =$ 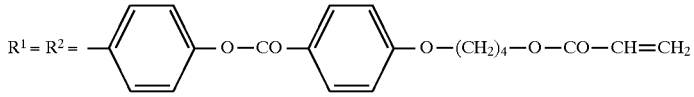 |
| 34 | $R^1 = R^2 =$  |

TABLE 7

The compounds can be synthesized by a method similar to that of Example 2.
chiral group:

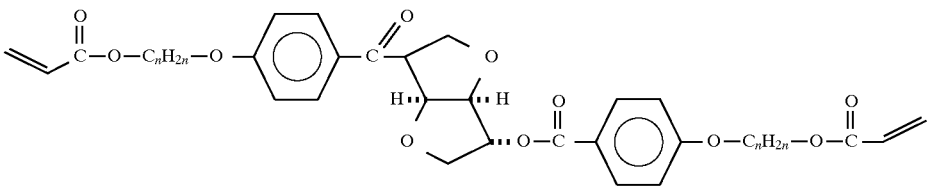

| | | |
|---|---|---|
| Example 35 | n = 4 | HTP: 41.5 μm$^{-1}$ |
| Example 36 | n = 6 | HTP: 44.7 μm$^{-1}$ |
| Example 37 | n = 8 | HTP: 47.7 μm$^{-1}$ |
| Example 38 | n = 11 | HTP: 52.3 μm$^{-1}$ |

HTP = helical twisting power
The compounds of Examples 39 to 42 are obtained by a procedure similar to that of Example 2 by reaction with methyl 4,6-benzylidene-α-D-glucopyranoside.

TABLE 8

| | chiral radical: |
|---|---|
| | 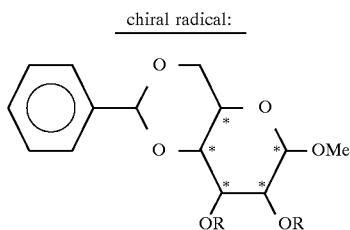 |
| Example | |
| 39 | 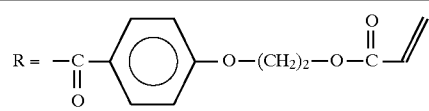 |
| 40 | 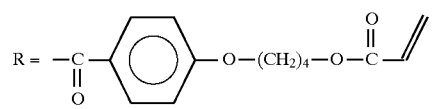 |
| 41 | 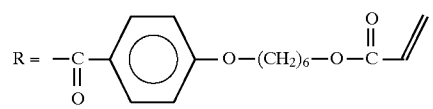 |
| 42 | 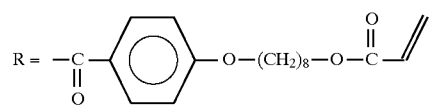 |

The compounds of Examples 43 to 47 are obtained by a method similar to that of Example 2 by reaction of the chiral radical with 4'-(ω-vinyloxy)alkyleneoxyphenyl-4-carboxylic acids.

| | chiral radical: |
|---|---|
| | 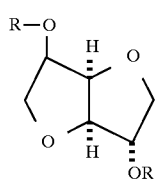 |
| Example | |
| 43 | 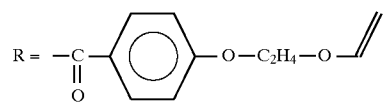 |
| 44 | 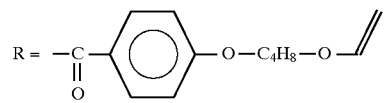 |
| 45 | 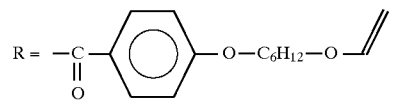 |
| 46 | 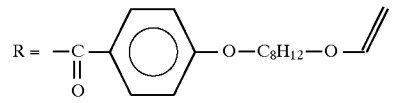 |

TABLE 8-continued

| 47 | 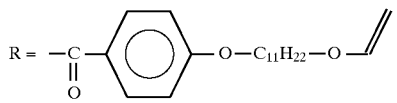 |
|---|---|

We claim:

1. A compound of the formula $$(Z-Y-A-Y-M-Y-)_n X \qquad I,$$

where, in each case independently of one another,

A is a spacer,

M is a group of the formula $(T-Y^1)_r-T$,

Y is a direct bond, O, S, COO, OCO, CON(R) or N(R)CO,

Z is a polymerizable group, n is a number from 2 to 6,

X is an optionally substituted chiral binaphthyl or biphenyl radical,

R is $C_1$- to $C_4$-alkyl or hydrogen,

T is cycloalkylene, an aromatic radical or a heteroaromatic radical, $Y^1$ is O, COO, OCO, $CH_2O$, $OCH_2$, CH=N, N=CH or a direct bond, and r is from 0 to 3.

2. A compound as claimed in claim 1, where r is 0 or 1.

3. A compound as claimed in claim 1, where n=2.

4. A compound as claimed in claim 1, where X is

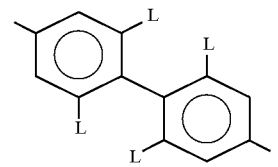

where

L is $C_1$- to $C_4$-alkyl, $C_1$–$C_4$-alkoxy, halogen, COOR, OCOR, CONHR or NHCOR, and R is as defined above.

5. A compound as claimed in claim 2, where X is

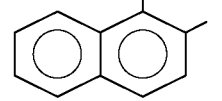

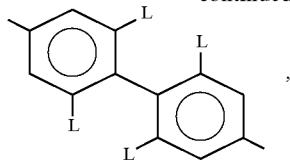

where

L is $C_1$- to $C_4$-alkyl, $C_1$–$C_4$-alkoxy, halogen, COOR, OCOR, CONHR or NHCOR, and R is defined above.

6. In a process for the preparation of a cholesteric, network the improvement comprising incorporating the compound of claim 1 therein as a polymerizable, chiral dope.

7. The polymerizable, chiral compound as claimed in claim 1, wherein A is a chain of 2–30 carbon atoms, optionally interrupted in the chain with O, S, NH or $NCH_3$, and optionally substituted on the chain with fluorine, chlorine, bromine, cyano, methyl or ethyl;

wherein T is selected from the group consisting of the following structures:

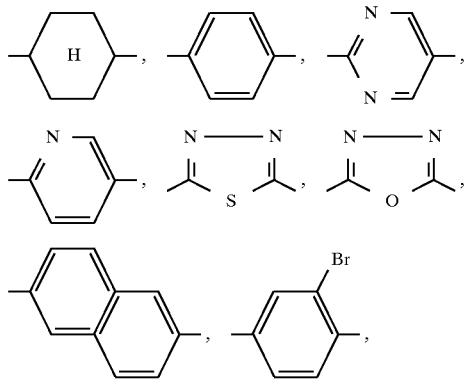

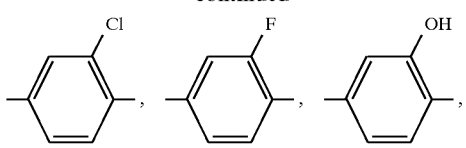

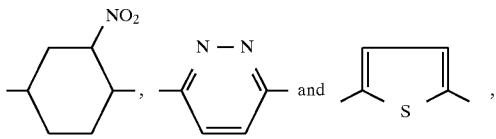

which structure may be unsubstituted or substituted by fluorine, chlorine, bromine, cyano, hydroxyl or nitro;

and wherein Z is selected from the group consisting of the following structures:

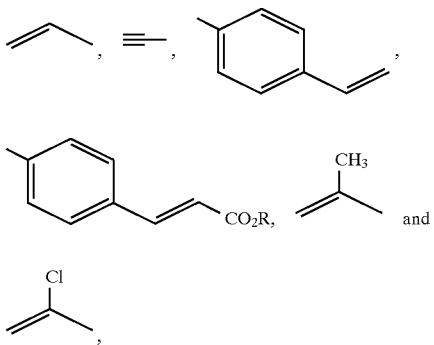

where R is defined above.

* * * * *